United States Patent
Auvray et al.

(10) Patent No.: US 12,133,809 B2
(45) Date of Patent: Nov. 5, 2024

(54) STENT POSITIONING

(71) Applicant: KONINKLIJKE PHILIPS N.V., Eindhoven (NL)

(72) Inventors: Vincent Maurice Andre Auvray, Meudon (FR); Raoul Florent, Ville D'Avray (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 783 days.

(21) Appl. No.: 17/252,748

(22) PCT Filed: Jun. 24, 2019

(86) PCT No.: PCT/EP2019/066619
§ 371 (c)(1),
(2) Date: Dec. 16, 2020

(87) PCT Pub. No.: WO2020/002201
PCT Pub. Date: Jan. 2, 2020

(65) Prior Publication Data
US 2021/0251787 A1   Aug. 19, 2021

(30) Foreign Application Priority Data
Jun. 28, 2018   (EP) .................................... 18290070

(51) Int. Cl.
*A61F 2/958*   (2013.01)
*A61B 6/00*   (2024.01)
(Continued)

(52) U.S. Cl.
CPC .............. *A61F 2/958* (2013.01); *A61B 6/469* (2013.01); *A61B 6/487* (2013.01); *A61B 90/39* (2016.02);
(Continued)

(58) Field of Classification Search
CPC .... A61B 2090/3966; A61B 2090/3983; A61B 6/469; A61B 6/487; A61B 6/504;
(Continued)

(56) References Cited

U.S. PATENT DOCUMENTS 9,345,597 B2    5/2016  Pacetti
2004/0260175 A1  12/2004  Florent et al.
(Continued)

FOREIGN PATENT DOCUMENTS

EP          620129 A2    7/2013
JP       2012081136 A    4/2012
(Continued)

OTHER PUBLICATIONS

PCT/EP/2019/066619, WO & ISR, Jul. 19, 2019, 16 Page Document.

*Primary Examiner* — Mohamed G Gabr

(57) ABSTRACT

The present invention relates to positioning of stents or other medical interventional devices. In order to provide an improved marker detection suitable for smaller markers, a device (10) for positioning a medical interventional device is provided. The device comprises a data input interface (12), a data processing unit (14) and a data output interface (16). The data input interface is configured to provide at least one image of a region of interest of a subject. In the at least one image, at least a part of a guiding apparatus for a medical interventional device is arranged in the region of interest, which part of the guiding apparatus comprises at least one apparatus position marker visible in the at least one image. Further, in the at least one image, a medical interventional device is arranged at least partly in the region of interest, which medical interventional device comprises device position markers, which are less visible in the image than the at least one apparatus position marker. The data processing unit is configured to detect the at least one (Continued)

apparatus position marker in the at least one image, and to define a proximity region in the at least one image based on the at least one apparatus position marker, and to select the proximity region, to detect the device position markers in the proximity region, and to enhance the device position markers in the at least one image for supporting a positioning of the medical interventional device. The data output interface is configured to provide the at least one image with the enhanced device position markers.

20 Claims, 7 Drawing Sheets

(51) Int. Cl.
 *A61B 6/46* (2024.01)
 *A61B 90/00* (2016.01)
(52) U.S. Cl.
 CPC ............... *A61B 2090/3966* (2016.02); *A61B 2090/3983* (2016.02)

(58) Field of Classification Search
 CPC ................... A61B 90/39; A61F 2/958; G06T 2207/10121; G06T 2207/30052; G06T 2207/30204; G06T 7/73
 See application file for complete search history.

(56) References Cited

U.S. PATENT DOCUMENTS

| | | |
|---|---|---|
| 2006/0265041 A1 | 11/2006 | Sanati et al. |
| 2008/0045827 A1* | 2/2008 | Rongen .................. A61B 6/504 600/407 |
| 2008/0267475 A1 | 10/2008 | Lendl |
| 2011/0144460 A1 | 6/2011 | Oh et al. |
| 2014/0079308 A1 | 3/2014 | Chen et al. |

FOREIGN PATENT DOCUMENTS

| | | |
|---|---|---|
| JP | 2017086413 A | 5/2017 |
| WO | 2014124447 A1 | 8/2014 |
| WO | 2017042068 A1 | 3/2017 |

* cited by examiner

STENT POSITIONING

CROSS-REFERENCE TO PRIOR APPLICATIONS

This application is the U.S. National Phase application under 35 U.S.C. § 371 of International Application No. PCT/EP2019/066619, filed on Jun. 24, 2019, which claims the benefit of European Patent Application No. 18290070.4, filed on Jun. 28, 2018. These applications are hereby incorporated by reference herein.

FIELD OF THE INVENTION

The present invention relates to positioning of stents or other medical interventional devices, and relates, in particular, to a device for positioning a medical interventional device, to a medical imaging system and to a method for positioning a medical interventional device, e.g. a stent, as well as to a computer program element for controlling an apparatus and a computer readable medium having stored the program element.

BACKGROUND OF THE INVENTION

In minimal invasive surgery, it is known to insert medical interventional devices like stents or other forms or prosthesis in a lumen, e.g. a vasculature or tissue structure of a subject, via a guiding apparatus like a guidewire. For correct placement of the medical interventional devices, the relative position of the medical interventional device must be determined. For this purpose, the current position of the device is determined and brought into relation to the subject. An example of a current position determination is the use of X-ray radiation for determining the relative position in an image of the region of interest. Other position determination may use electromagnetic waves for locating position markers inside the subject and to register these positions with image data of the data. For indicating the current position of medical interventional devices that are hardly visible by themselves, or even invisible, in X-ray images, device markers may be used that are visible in X-ray. However, it has been shown that even device marker detection can be cumbersome, for example due to a demand for small-sized structures of the devices resulting also in smaller markers. An example for such smaller markers are provided for example on bioresorbable stents.

SUMMARY OF THE INVENTION

There may thus be a need for an improved marker detection suitable for smaller and less X-ray visible markers.

The object of the present invention is solved by the subject-matter of the independent claims; further embodiments are incorporated in the dependent claims. It should be noted that the following described aspects of the invention apply also for the device for positioning a medical interventional device, for the medical imaging system and for the method for positioning a medical interventional device.

According to the present invention, a device for positioning a medical interventional device is provided. The device comprises a data input interface, a data processing unit, and a data output interface. The data input interface is configured to provide at least one image of a region of interest of a subject. In the at least one image, at least a part of a guiding apparatus for a medical interventional device is arranged in the region of interest, which part of the guiding apparatus comprises at least one apparatus position marker visible in the at least one image. Further, in the at least one image, a medical interventional device is arranged at least partly in the region of interest, which medical interventional device comprises device position markers that are less visible in the image than the at least one apparatus position marker. The data processing unit is configured to detect the at least one apparatus position marker in the at least one image, and to define a proximity region in the at least one image based on the at least one apparatus position marker. The data processing unit is also configured to select the proximity region, to detect the device position markers in the proximity region, and to enhance the device position markers in the at least one image for supporting a positioning of the medical interventional device. The data output interface is configured to provide the at least one image with the enhanced device position markers.

The medical interventional device can be, for example, a stent to be inserted in a vasculature or organ or tissue structure. The medical interventional device can also be, as further example, a prosthesis, such as an artificial heart valve.

As an advantage, the detection of the device position markers is provided only for a selected part of the image of the region of interest. The selected part can then be subject to a more detailed search, resulting in an increased accuracy as well as a lower risk to detect false positives. Thus, the selection of the part of the image also allows to look for smaller markers. By defining a selected part of the image for the device position markers, it is also possible to reduce the device detection effort.

The term "proximity region" relates to a region around the detected item, i.e. a region nearby the item. The proximity region can also be referred to as neighboring or surrounding region. The size, or extension, of the proximity region may be determined, or selected, or chosen, according to a range in which the location of the (smaller) device position markers are to be found. The proximity region is determined such that as a result only a smaller part of the whole image is selected, e.g. resulting in less than half of the image, e.g. a third or fourth or fifth of the image. In an example, the proximity region is less than a tenth of the image. In another example, the proximity region is less than 5% of the image, e.g. less than 1%.

A "guiding apparatus" may be understood as any apparatus or device, or part thereof, which is usable to guide and/or carry a medical interventional device. For example, for a stent as a medical interventional device, a guiding apparatus may comprise one or more of a guidewire, a stent balloon or a balloon catheter.

According to an example, the data input interface is configured to provide the at least one image with a stent as the medical interventional device arranged at least partly in the region of interest.

According to an example, the data processing unit is configured to define the proximity region as an area around the at least one apparatus position marker.

According to an example, the guiding apparatus also comprises a guidewire, and the data processing unit is configured to define the proximity region as an image area with a longitudinal expansion direction along the guidewire.

According to the present invention, also a medical imaging system is provided. The system comprises an imaging device with an X-ray source and an X-ray detector, and a device for positioning a medical interventional device according to one of the preceding examples. The imaging device is configured to generate the at least one image of a region of interest of a subject.

In an option, the images are fluoroscopic images.

The medical imaging system can also be referred to as interventional imaging system.

According to an example, the system further comprises a guiding apparatus for a medical interventional device, the guiding apparatus comprising the at least one apparatus position marker. The system further comprises a medical interventional device, the medical interventional device comprising the device position markers.

In an option, the medical interventional device is a stent to be deployed and the device position markers are stent position markers. The guiding apparatus is a stent guiding device and the at least one apparatus position marker is at least one guiding device position marker.

According to an example, the stent guiding device is a balloon device to which the to-be-deployed stent is attached. The at least one guiding device position marker is a balloon marker. The data processing unit is configured to define the proximity region based on the at least one balloon marker.

According to the present invention, also a method for positioning a medical interventional device is provided. The method comprises the following steps:

a) providing at least one image of a region of interest of a subject;

b1) detecting, in the at least one image, at least one apparatus position marker of a guiding apparatus for a medical interventional device at least partly being arranged in the region of interest;

b2) defining a proximity region in the at least one image based on the at least one apparatus position marker;

c1) selecting the proximity region;

c2) detecting, in the proximity region, device position markers of the medical interventional device at least partly being arranged in the region of interest, the device position markers being less visible in the image than the at least one guiding apparatus marker; and d) enhancing the device position markers in the at least one image for supporting a positioning of the medical interventional device.

In an example, the method is applied for a percutaneous coronary intervention (PCI). For example, a bioresorbable stent (BVS) is used.

In another example, the invention uses other proximities, e.g. other guiding or support tools for a medical interventional device. Hence, other objects than stent markers are be detected.

According to an example, the medical interventional device is a stent to be deployed, and the device position markers are stent position markers. Further, the guiding apparatus is a stent guiding device, and the apparatus position marker is a device position marker.

In an option, the stent guiding device is a balloon device to which the to-be-deployed stent is attached, and the at least one device position marker is a balloon marker. The proximity region is defined based on the at least one balloon marker.

According to an example, the proximity region is defined as an area around the at least one apparatus position marker. In addition, or alternatively, the guiding apparatus also comprises a guidewire, and the proximity region is defined as an image area with a longitudinal expansion direction along the guidewire.

According to an example, a sequence of images is provided. Steps b1) to c2) are provided for each of the images. Further, before step d), a step is provided in which the images are temporally registered based on the respectively detected device position markers, which provides a temporal boost of the images. The images are centered relative to each other based on: i) the detected device position markers, or ii) the at least one detected apparatus position marker.

According to an aspect, image data is provided of a region of interest in which a device like a stent is assumed that is to be located and exactly positioned. However, the device is difficult to detect in the image data of the region of interest. As a first detection approach for locating the device, an indicator is detected that is considered to relate to a part of the image in which the device is arranged. The indicator is chosen as a structure or feature that is easier to detect in the image data of the region of interest than the device. Based on the indicator, the part of the image is selected. As a second detection approach, the selected part of the image is then taken for detecting the device itself. Hence, the image of the region of interest is divided into a part that is of more detailed interest for the device location and a part that is not further used for the device location. The detection of the device is provided only for a selected part of the image of the region of interest.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
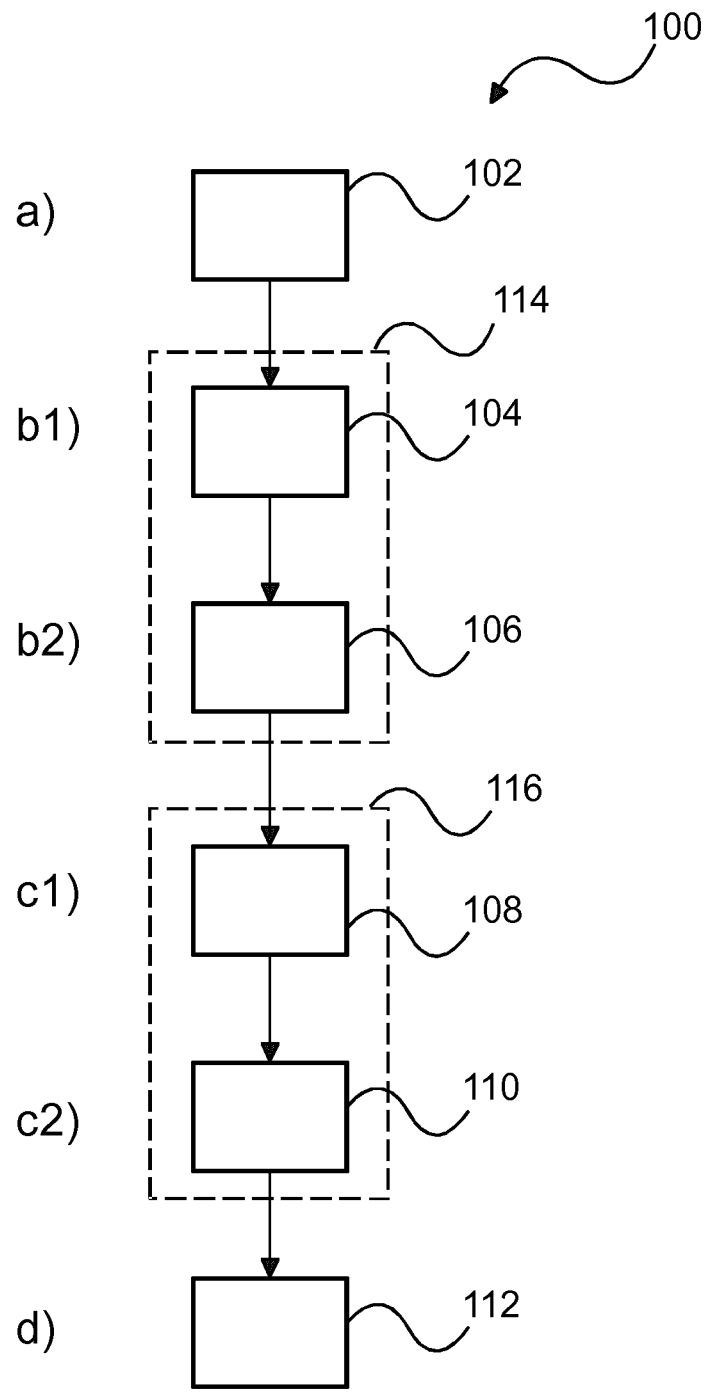
FIG. 1 shows steps of an example of a method for positioning a medical interventional device.

In FIG. 1, an example of a method 100 for positioning a medical interventional device is shown. The method 100 comprises the following steps:

In a first step 102, also referred to as step a), at least one image of a region of interest of a subject is provided. In the at least one image, at least a part of a guiding apparatus for the medical interventional device is arranged in the region of interest, which part of the guiding apparatus comprises at least one apparatus position marker visible in the at least one image. Further, in the at least one image, a medical interventional device is arranged at least partly in the region of interest, which medical interventional device comprises device position markers, which are less visible in the image than the at least one guiding apparatus marker.

In a second step 104, also referred to as step b1), the at least one apparatus position marker is detected in the at least one image.

In a third step 106, also referred to as step b2), a proximity region is defined in the at least one image based on the at least one apparatus position marker.

In a fourth step 108, also referred to as step c1), the proximity region is selected.

In a fifth step 110, also referred to as step c2), the device position markers are detected in the proximity region.

In a sixth step 112, also referred to as step d), the device position markers are enhanced in the at least one image for supporting a positioning of the medical interventional device.

The second step b1) and the third step b2) can be considered as respective first and second sub-steps of a first detection step b), indicated with a hashed first frame 114, provided for the complete at least one image.

The fourth step c1) and the fifth step c2) can be considered as respective first and second sub-steps of a second detection step c), indicated with a hashed second frame 116, provided for the selected region, i.e. the proximity region, also referred to a proxy-region.

Figure 2:
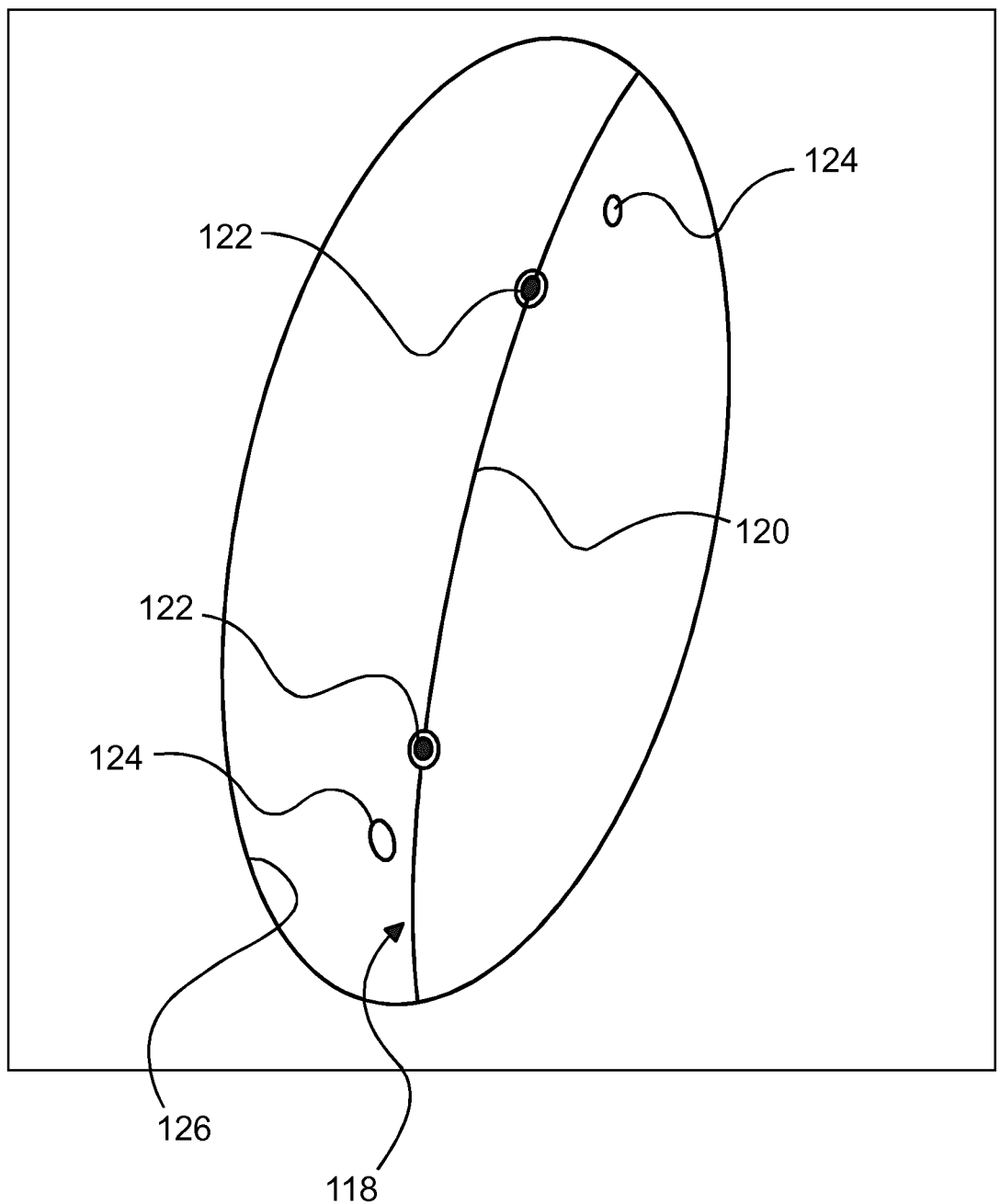
FIG. 2 shows an X-ray image of a stent as an example for a medical interventional device and a balloon as an example for a device for positioning the stent.

In FIG. 2, an X-ray image 118 of a stent as an example for a medical interventional device is shown. A guidewire 120 is shown that acts as the guiding and inserting device. A balloon is provided as an example for a device for positioning the stent. The balloon is provided on the guidewire and is indicated with two position markers 122 that are also referred to as balloon markers. The stent is arranged on the balloon, and with inflation of the balloon, the stent can be expanded and brought into position and place. The stent is indicated with two hardly visible stent markers 124. The stent may be provided as a bioresorbable stent. The X-ray image 128 may be a collimated fluoroscopic image of a region of interest taken live during examination for supporting in positioning of the stent. The collimation may be provided, for example, in form an elliptic diaphragm.

In an example of the method, not further shown in detail, the medical interventional device is a stent to be deployed and the device position markers are stent position markers. The guiding apparatus is a stent guiding device and the apparatus position marker is a device position marker. As an option, it is provided that the stent guiding device is a balloon device to which the to-be-deployed stent is attached. The at least one device position marker is a balloon marker. The proximity region is defined based on the at least one balloon marker.

The device for positioning a medical interventional device can also be referred to as device for positioning a stent.

If the medical interventional device is provided as a stent, or as two or more stents, the device position markers are provided as stent markers.

In an example, the stent is a bioresorbable stent. It is noted that bioresorbable stents (BVS) may be beneficial for a long-term outcome of stenosis treatment, for example. Bioresorbable stents may be used when treating long stenosis e.g. in young subjects. Treating long regions may imply successively implanting several bioresorbable stents. The detection of the markers based on the proximity definition provides e.g. facilitated placing stents with respect to each other. As an advantage, stents can be positioned close enough in order to completely cover an artery, while minimally overlapping in order not to hermetically cover a part of the vessel. Even though a bioresorbable stent may be transparent (or at least close to transparent) to X-rays, a minimal overlap of adjacent stents can be achieved by placing a distal marker of a stent next to a proximal marker of the neighboring stent, resulting in less than e.g. 1 mm of overlap.

Despite that markers of bioresorbable stents may be so small that directly detecting them in the image is close to impossible, by selecting the proximity area first, the detection of the stent markers is achieved.

In an aspect, the (larger and more contrasted) balloon markers are detected in a first step, and then, in a second step, the (smaller and fainter) markers of the stent itself are looked for in the vicinity of the balloon markers.

As a result, a view may be presented to the user superior to using existing stent-boost technology only. Hence, in an example, blur-free images are provided even while the balloon position is being readjusted, resulting in a smooth and comfortable stent positioning, for example. This is, in particular, useful for situations where a stent does not move with the exact same motion than the balloon markers, which is all the more likely the further away stent markers and balloon markers are.

The two-step detection procedure facilitates the use of smaller markers for the stent. The two-step detection procedure also allows the use of lower dose X-ray radiation. It also allows to have the target region presented centrally, with the steered object moving with respect to it, which is also more intuitive.

The two-step detection also provides that, even when the stent completely fades away as the clinician reposition her/his balloon, and no structure is moving coherently with the balloon marker, the stent position is indicated.

The clinician is provided with support in the gesture with the solution centered on e.g. the stent markers, that enhances them constantly, for example by means of boosting, highlighting and/or stabilizing.

In an example, it is proposed to rely on the proximity to perform the detection of the stent markers, namely to proceed in two steps: to identify a proximity close to the structure of interest, which is easier to detect. For example, these could be the (larger and more contrasted) balloon markers; and, to look for barely detectable structures of interest in its vicinity, e.g. (small and faint) stent markers. Once this detection has been achieved, enhancing solutions e.g. highlighting, boosting or stabilizing can be provided.

The device for positioning a stent can also be referred to as a device for determining the position of a stent, or as a device for supporting positioning of a stent.

The data input interface can also be referred to as image data input interface. The data output interface can also be referred to as image data output interface.

In a further example of the method, also not further shown in detail, the proximity region is defined as an area around the at least one apparatus position marker.

In a further example of the method, also not further shown in detail, provided in addition or alternatively, the guiding apparatus also comprises a guidewire and the proximity region is defined as an image area with a longitudinal expansion direction along the guidewire.

Figure 3:
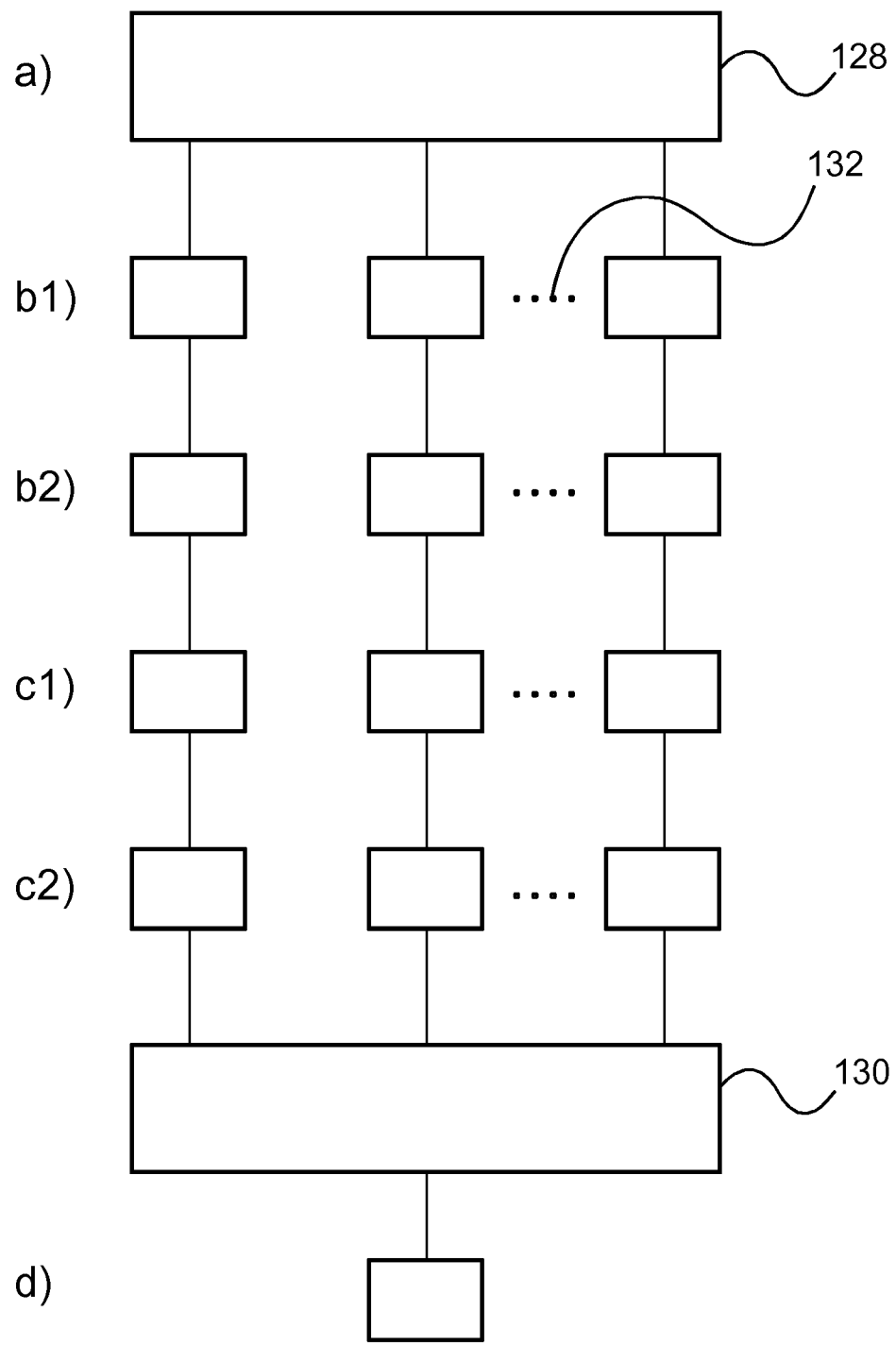
FIG. 3 shows another example of a method for positioning a medical interventional device.

In FIG. 3, a further example of a method for positioning a medical interventional device is shown. In step a), a sequence of images is provided 128. The steps b1) to c2) are provided for each of the images, as indicated with dotted lines 132. Before step d), a step is provided, in which the images are temporally registered 130 based on the respectively detected device position markers, which provides a temporal boost of the images. For example, the images are centered relative to each other based on: i) the detected device position markers; or ii) the at least one detected apparatus position marker.

Figure 4:
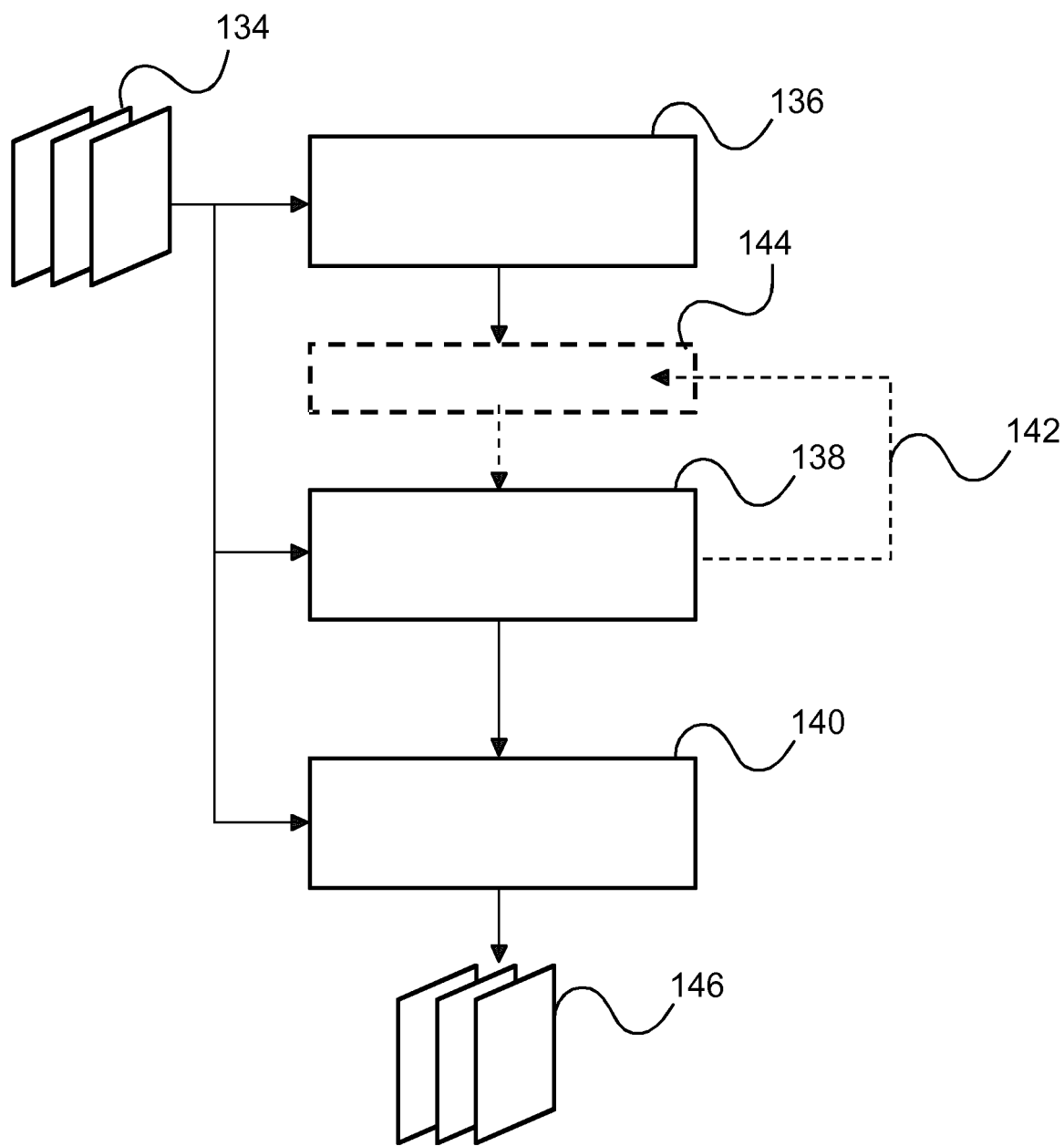
FIG. 4 shows a further example of a method for positioning a medical interventional device.

In FIG. 4, a still further example of a method for positioning a medical interventional device is shown. Fluoroscopic images are provided 134 as input.

One or several so-called proxy objects are detected 136 over the first frames, which allows to define a region in the respective image, i.e. a tight region where to look for poorly visible, e.g. faint markers. The term "proxy objects" refers to objects that are easily detectable to provide a basis for defining the region within the image that is then selected for a more detailed search for detecting the actual markers of interest. Proxy objects may be, for example, markers of a catheter, markers of a balloon or a guidewire present in the images. The defined region is also referred to as BVS region. An example for the actual, poorly visible markers are makers of bioresorbable stents (BVS markers).

A specific detector finds, i.e. detects 138 the position of the BVS markers in this region.

The detected BVS markers are then used to enhance 140 the bioresorbable stents (BVS).

Once the first images have been processed, a temporal consolidation 142 can be exploited to define the BVS region of interest (basically, the BVS markers are expected to remain close to their last detected position). This option is indicated with a hashed line. The temporal consolidation can substitute or complement the proxy-based region, as indicated with a dotted frame 144.

In the proxy-based definition 136 of the BVS region, objects are detected that give a good indication of the expected position of the object of interest—and which are easier to detect. In an example, the balloon markers are particularly interesting in case of multi-stent branch stenting, since they are expected to be close to the deployed (or to-be-deployed) BVS. The clinician has no trouble to steer the balloon in the approximate region of deployment, since she/he knows well which vessel segment she/he has just stented, i.e. which region has been entered with the catheter where a stent is applied. However, there is need for the final accurate positioning.

Detecting balloon markers as object of a lot of research is a crucial building box in application of enhancing stents, e.g. in the so-called stent boost application. Balloon markers can be found by designing filters that enhance them, and then developing smart tracking algorithms. Alternatively, one can train a marker detector using machine learning techniques.

One can deduct from the proxy position the possible position of the BVS markers. A crude region would simply be formed a couple of circles centered around the balloon markers.

The region could be made anisotropic by exploiting the balloon direction, which gives a good estimation of the local vessel orientation. The search region could then be formed of two ellipses centered around both detected balloon markers, and elongated in the direction defined by the markers.

One could also detect the guidewire (close to the balloon markers), and define the region of research as being in the vicinity of the guide wire.

In the BVS markers detection 140, it is possible to focus on a reduced region, i.e. a region within the image but smaller than the overall image. Whatever the details of the chosen region definition, it is focused on a tight region, in which the BVS markers are expected.

The task of detecting these small faint markers, which is close to impossible when considering the entire image, becomes doable. Detecting objects as markers is then provided as a trade-off between accuracy and false alarms. Now that the search region has been reduced by a factor lying somewhere e.g. between 100 and 10000 (in surface), a larger false positive rate can be afforded, and it is provided to reliably find the BVS markers. To perform this, hand-crafted features highlighting the BVS markers are manually designed. In another option detectors are provided that learn by using a machine learning method such as deep Learning.

Moreover, the temporal consolidation 142 can be exploited. The shape, orientation and position of the markers can progressively be learned, and the detection improved. After a few frames, it can be that the expected shape and position of the BVS markers, learned by the BVS detector, is sufficiently well defined to ensure a robust detection by itself, so that for further steps, the proximity region definition is thereby replaced. However, for initialization, the proxy detection is provided.

In the BVS highlighting 140, enhanced images 146 are generated that are also referred to as boosted images. For this purpose, once the BVS markers have been enhanced, a number of visualization modes can be provided to help the clinician in her/his operation, i.e. gesture.

One example provides a BVS-marker-boost. However, the boosting process is centered on the BVS markers instead of balloon markers. This results in that the BVS markers are spatially sharp, since the view would be centered on them, and the BVS markers' sharpness stays unaffected by sliding movements of the balloon markers. This allows for a comfortable and smooth positioning of the balloon.

Figure 5:
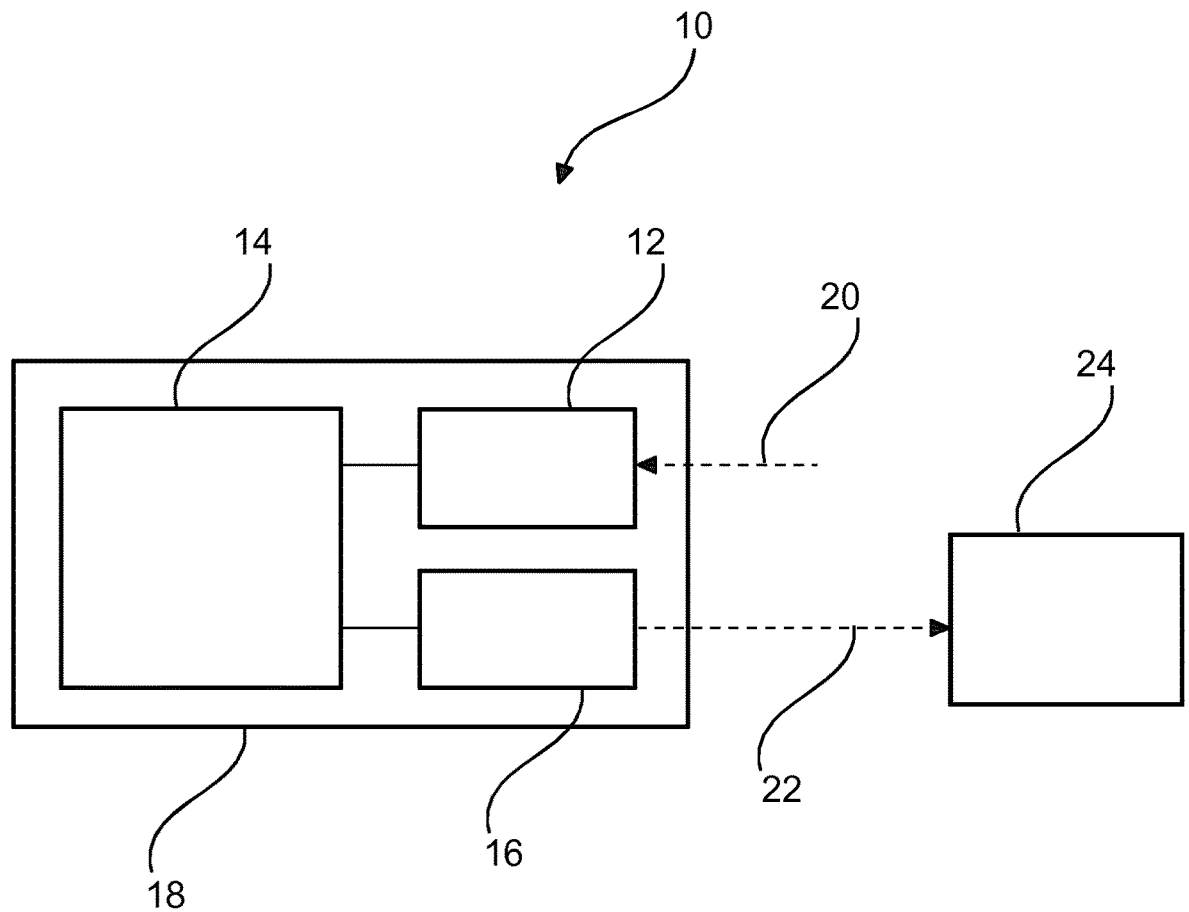
FIG. 5 schematically illustrates an example of a device for positioning a medical interventional device.

Alternatively, it is provided that the view is centered on the balloon markers, but with a temporal boost performed based on the BVS markers. In other words, the view is the same as the previous one (same boosting, same spatial and temporal BVS sharpness), except that it is finally centered on the balloon markers. This is intended for clinicians who are used to the "stentboost" view, and who would prefer to stay in the same referential. In an option, the BVS markers are colored, either on the original image or on the boosted image. In FIG. 5, an example of a device 10 for positioning a medical interventional device is schematically illustrated. The device 10 comprises a data input interface 12, a data a data processing unit 14 and a data output interface 16. The data input interface 12 is configured to provide at least one image of a region of interest of a subject. In the at least one image, at least a part of a guiding apparatus for a medical interventional device is arranged in the region of interest, which part of the guiding apparatus comprises at least one apparatus position marker visible in the at least one image. Further, in the at least one image, a medical interventional device is arranged at least partly in the region of interest, which medical interventional device comprises device position markers, which are less visible in the image than the at least one apparatus position marker. The data processing unit 14 is configured to detect the at least one apparatus position marker in the at least one image. The data processing unit 14 is also configured to define a proximity region in the at least one image based on the at least one apparatus position marker. The data processing unit 14 is still further also configured to select the proximity region, to detect the device position markers in the proximity region, and to enhance the device position markers in the at least one image for supporting a positioning of the medical interventional device. The data output interface 16 is configured to provide the at least one image with the enhanced device position markers.

The provided image data is indicated with a first hashed-line arrow 20, the output data is indicated with a second hashed-line arrow 22.

In an example, not further shown in detail, the data input interface 12 is configured to provide the at least one image with a stent as the medical interventional device arranged at least partly in the region of interest.

In FIG. 5, an example is shown as an option, in which a display unit 24 is provided configured to present the at least one image of a region of interest with enhanced device position markers.

In an example, not further shown in detail, the data processing unit is configured to define the proximity region as an area around the at least one apparatus position marker.

In an example, not further shown in detail, the guiding apparatus also comprises a guidewire, and the data processing unit 14 is configured to define the proximity region as an image area with a longitudinal expansion direction along the guidewire. In an example, not further shown in detail, the data input interface 12 is configured to provide a sequence of images. The data processing unit 14 is configured to detect the at least one apparatus position marker. The data processing unit 14 is configured to define a proximity region based on the at least one apparatus position marker, to select the proximity region, and to detect the device position markers in the proximity region for each of the images. The data processing unit 14 is also configured to temporally consolidate the images based on the respectively detected device position markers, which provides a temporal boost of the images. The data processing unit 14 is further configured to center the images relative to each other based on i) the detected device position markers, or based on ii) the at least one detected apparatus position marker.

Figure 6:
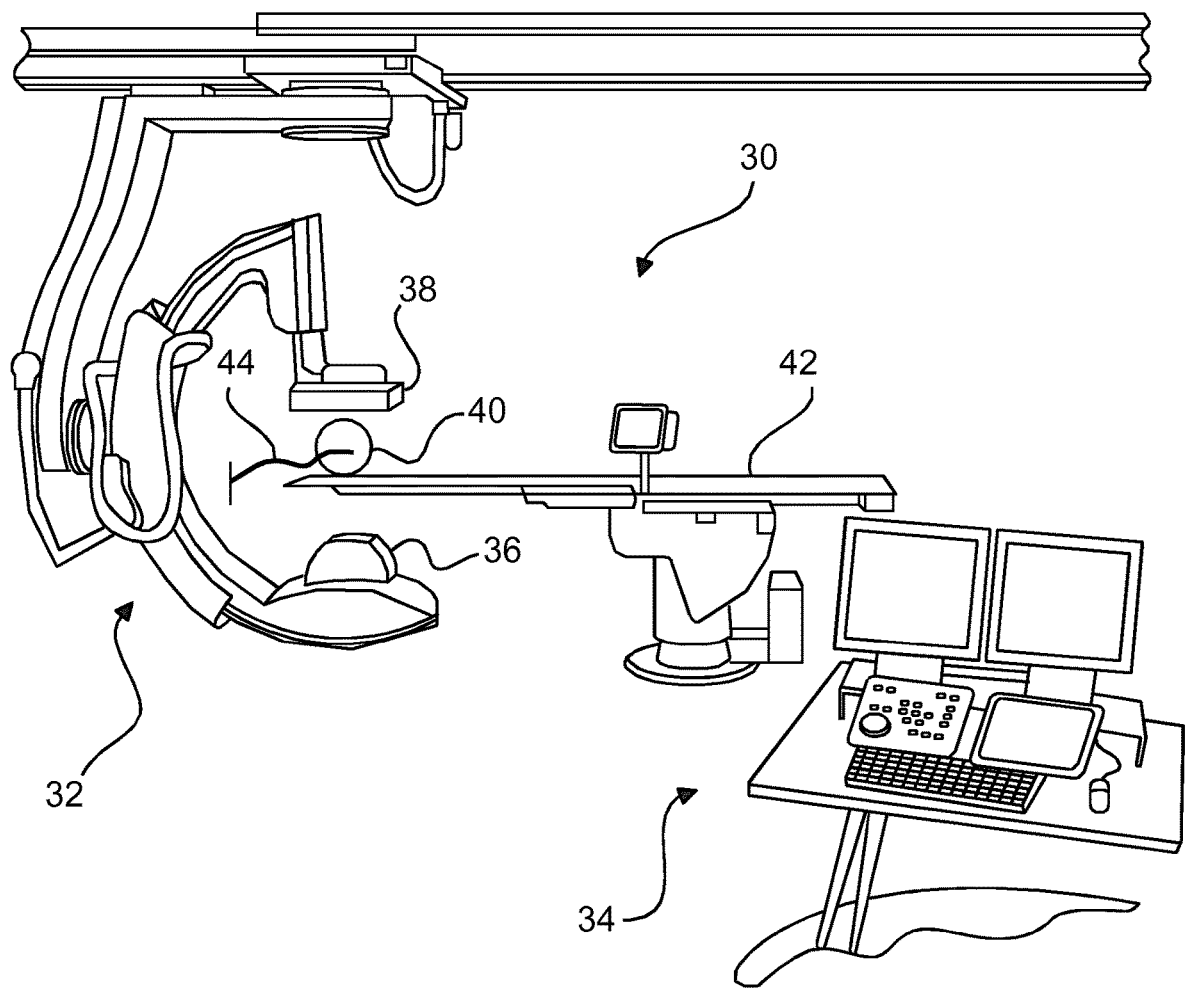
FIG. 6 schematically illustrates an example of a medical imaging system.

In FIG. 6, an example of a medical imaging system 30 is schematically illustrated. The medical imaging system 30 comprises an imaging device 32 with an X-ray source 36 and an X-ray detector 38. The medical imaging system 30 also comprises a device 34 for positioning a medical interventional device according to one of the preceding examples. The imaging device 32 is configured to generate the at least one image of a region of interest of a subject. As an option, the images are fluoroscopic images.

The imaging device 32 may be provided as a C-arc X-ray system. The example shows a C-arc suspended from the ceiling, but also floor-mounted or even mobile X-ray imaging systems are provided.

An object of interest, i.e. a subject, is indicated schematically with a circle 40. The subject may be arranged on a patient table 42.

As an option, it is shown that the system 30 further comprises a guiding apparatus 44 for a medical interventional device, the guiding apparatus 44 comprising the at least one apparatus position marker. The system 30 further comprises a medical interventional device, the medical interventional device comprising the device position markers.

As an option, the medical interventional device is a stent to be deployed and the device position markers are stent position markers. Further, the guiding apparatus is a stent guiding device and the at least one apparatus position marker is at least one guiding device position marker.

In an example, the stent guiding device is a balloon device to which the to-be-deployed stent is attached. The at least one guiding device position marker is a balloon marker. The data processing unit is configured to define the proximity region based on the at least one balloon marker.

Figure 7:
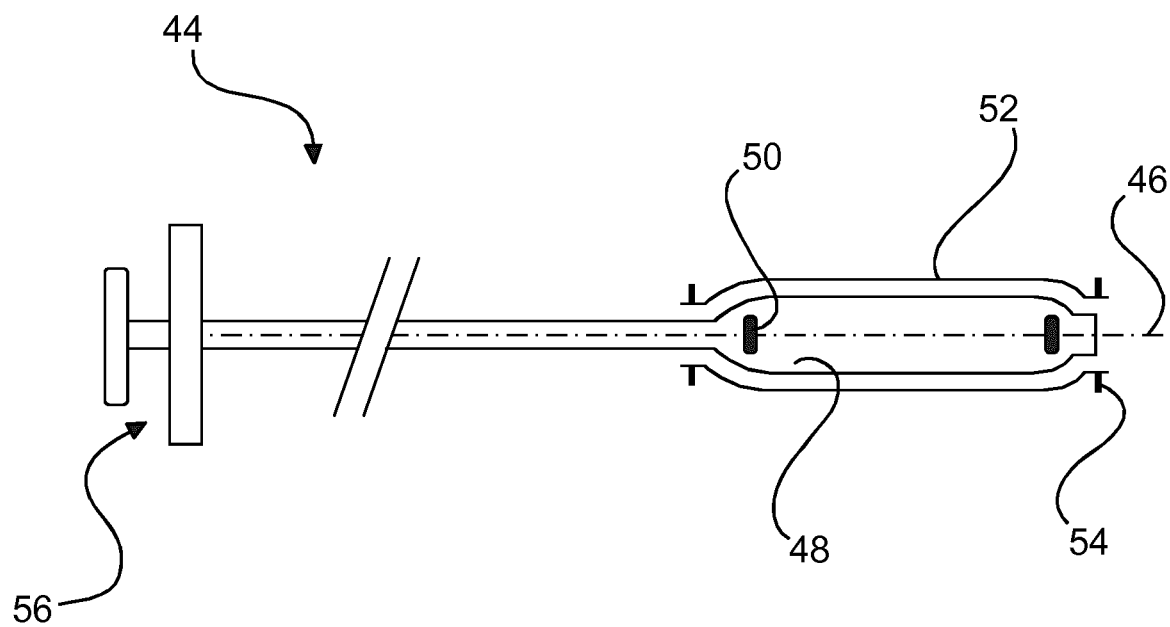
FIG. 7 schematically illustrates a catheter with a balloon and a stent.

In FIG. 7, a catheter device 44 is shown. A hashed line indicates a guidewire 46. A balloon 48 with balloon markers 50 is provided. Further, a stent 52 with stent markers 54 is shown. A handle 56, or grip portion, is schematically indicated. The stent markers 54 are less visible in X-ray images than the balloon markers 50.

The detection of the less visible stent markers 54 is provided by a detection that is restricted to a region, i.e. part of the image. The restriction is based on the detection of the better visible balloon markers 50, since the stent markers are assumed to be arranged near the balloon markers.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for supporting positioning of a medical interventional device, the device comprising:
   input circuitry configured to provide an image of a region of interest of a subject;
   a processor configured to:
   detect, in the image, at least one apparatus position marker disposed on a guiding apparatus for the medical interventional device at least partly arranged in the region of interest;
   define a proximity region in the image based on the at least one apparatus position marker;
   select a part of the image defined by the proximity region;
   detect, in the selected part of the image, one or more device position markers of the medical interventional device,
   enhance the one or more device position markers in the image for supporting the positioning of the medical interventional device, wherein the one or more device position markers are less visible in the image than the at least one apparatus position marker, and
   provide the image with the enhanced one or more device position markers.

2. The device according to claim 1, wherein the input circuitry is configured to provide the image with a stent as the medical interventional device arranged at least partly in the region of interest.

3. The device according to claim 1, further comprising a display configured to present the image of the region of interest with the enhanced one or more device position markers.

4. The device according to claim 1, wherein the processor is further configured to define the proximity region as an area around the at least one apparatus position marker.

5. The device according to claim 1, wherein:
   the guiding apparatus comprises at least one of a guidewire, a balloon, and a catheter; and
   the processor is configured to define the proximity region as an image area with a longitudinal expansion direction along the guiding apparatus.

6. The device according to claim 1, wherein:
   the input circuitry is configured to provide the image as a part of a sequence of images;
   the processor is configured to:
   detect the at least one apparatus position marker;
   define the proximity region based on the at least one apparatus position marker;
   select the proximity region; and
   detect the one or more device position markers in the proximity region for each of the images of the sequence of images;
   temporally consolidate the images based on the respectively detected one or more device position markers, which provides a temporal boost of the images; and
   center the images relative to each other based on i) the detected one or more device position markers; or ii) the at least one detected apparatus position marker.

7. The device according to claim 1, wherein the image is part of a sequence of image, and the processor is further configured to:
   for each respective image of the sequence of images:
   detect, in the respective image, at least one apparatus position marker disposed on the guiding apparatus for the medical interventional device at least partly arranged in the region of interest;
   define a proximity region in the respective image based on the at least one apparatus position marker;
   select a part of the respective image defined by the proximity region;
   detect, in the selected part of the respective image, one or more device position markers of the medical interventional device,
   enhance the one or more device position markers in the respective image for supporting the positioning of the medical interventional device, wherein the one or more device position markers are less visible in the respective image than the at least one apparatus position marker, and
   provide the respective image with the enhanced one or more device position markers.

8. A medical imaging system, comprising:
   an imaging device with an X-ray source and an X-ray detector; and
   the device for supporting the positioning of the medical interventional device according to claim 1;
   wherein the imaging device is configured to generate the image of the region of interest of the subject.

9. The medical imaging system according to claim 8, further comprising:
   the guiding apparatus for the medical interventional device, the guiding apparatus comprising the at least one apparatus position marker; and
   a stent to be deployed as the medical interventional device, the stent comprising one or more stent position markers,
   wherein the guiding apparatus is a stent guiding device and the at least one apparatus position marker is at least one guiding device position marker.

10. The medical imaging system according to claim 9, wherein:
    the stent guiding device is a balloon device to which the to-be-deployed stent is attached;
    the at least one guiding device position marker is a balloon marker; and
    the processor is configured to define the proximity region based on the balloon marker.

11. A method for supporting positioning of a medical interventional device, the method comprising:
    providing an image of a region of interest of a subject;

detecting, in the image, at least one apparatus position marker disposed on a guiding apparatus for the medical interventional device at least partly being arranged in the region of interest;

defining a proximity region in the image based on the at least one apparatus position marker;

selecting a part of the image defined by the proximity region;

detecting, in the selected part of the image, one or more device position markers of the medical interventional device, the one or more device position markers being less visible in the image than the at least one apparatus position marker; and enhancing the one or more device position markers in the image for supporting the positioning of the medical interventional device.

12. The method according to claim 11,
wherein the image is a part of a sequence of images and the method further comprising temporally registering the images based on the respectively detected one or more device position markers, which provides a temporal boost of the images.

13. The method according to claim 12, further comprising centering the images of the sequence relative to each other based on:
  i) the detected one or more device position markers; or
  ii) the at least one detected apparatus position marker.

14. The method according to claim 11, further comprising defining the proximity region as an area around the at least one apparatus position marker.

15. A non-transitory computer-readable storage medium having stored therein a computer program having instructions which, when executed by a processor, cause the processor to:
  obtain an image of a region of interest of a subject;
  detect, in the image, at least one apparatus position marker disposed on a guiding apparatus for a medical interventional device at least partly arranged in the region of interest;
  define a proximity region in the image based on the at least one apparatus position marker;
  select a part of the image defined by the proximity region;
  detect, in the selected part of the image, one or more device position markers of the medical interventional device;
  enhance the one or more device position markers in the image for supporting a positioning of the medical interventional device, wherein the one or more device position markers are less visible in the image than the at least one apparatus position marker; and
  provide the image with the enhanced one or more device position markers.

16. The non-transitory computer-readable storage medium according to claim 15, wherein:
  the instructions, when executed by the processor, further cause the processor to:
  obtain the image as part of a sequence of images, and
  temporally register the sequence of images based on the respectively detected one or more device position markers, which provides a temporal boost of the images.

17. The non-transitory computer-readable storage medium according to claim 16, wherein the instructions, when executed by the processor, further cause the processor to center the images of the sequence of images relative to each other based on:
  i) the detected one or more device position markers; or
  ii) the at least one detected apparatus position marker.

18. The non-transitory computer-readable storage medium according to claim 15, wherein the image is obtained with a stent as the medical interventional device arranged at least partly in the region of interest.

19. The non-transitory computer-readable storage medium according to claim 15, wherein the instructions, when executed by the processor, further cause the processor to define the proximity region as an area around the at least one apparatus position marker.

20. The non-transitory computer-readable storage medium according to claim 15, wherein the instructions, when executed by the processor, further cause the processor to:
  obtain the image as part of a sequence of images;
  detect the at least one apparatus position marker;
  define the proximity region based on the at least one apparatus position marker;
  select the proximity region and detect the one or more device position markers in the proximity region for each of the sequence of images;
  temporally consolidate the images based on the respectively detected one or more device position markers, which provides a temporal boost of the images; and
  center the images of the sequence of image relative to each other based on i) the detected one or more device position markers; or ii) the at least one detected apparatus position marker.

\* \* \* \* \*